(12) United States Patent
Jansen et al.

(10) Patent No.: US 6,520,935 B1
(45) Date of Patent: *Feb. 18, 2003

(54) SYRINGE AND TIP CAP ASSEMBLY

(75) Inventors: Hubert Jansen, Poisat (FR); Claude Imbert, La Tronche (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 269 days.

This patent is subject to a terminal disclaimer.

(21) Appl. No.: 09/643,348

(22) Filed: Aug. 22, 2000

Related U.S. Application Data

(63) Continuation of application No. 09/198,978, filed on Nov. 24, 1998, which is a continuation-in-part of application No. 08/847,840, filed on Apr. 28, 1997, now Pat. No. 6,027,482, which is a continuation of application No. 08/355,447, filed on Dec. 12, 1994, now Pat. No. 5,624,402.

(51) Int. Cl.[7] ................................................ A61M 5/00

(52) U.S. Cl. ...................................................... 604/111

(58) Field of Search ................................ 604/110, 111, 604/195, 198, 240–243, 263

(56) References Cited

U.S. PATENT DOCUMENTS

| | | |
|---|---|---|
| 1,727,755 A | 9/1929 | Dickinson |
| 1,742,497 A | 1/1930 | Dickinson |
| 1,793,068 A | 2/1931 | Dickinson |
| 2,158,593 A | 5/1939 | Scrimgeour |
| 2,371,086 A | 3/1945 | Watson et al. |
| 2,677,374 A | 5/1954 | Burnside |
| 2,755,801 A | 7/1956 | Morando |
| 2,764,978 A | 10/1956 | Everett |
| 2,811,155 A | 10/1957 | Dunnican |
| 3,491,757 A | 1/1970 | Arce |
| 4,043,334 A | 8/1977 | Brown et al. |
| 4,187,848 A * | 2/1980 | Taylor ........................ 604/243 |
| 4,266,815 A | 5/1981 | Cross |
| 4,597,758 A | 7/1986 | Aalto et al. |
| 4,636,201 A | 1/1987 | Ambrose et al. |
| 4,676,530 A | 6/1987 | Nordgren et al. |
| 4,747,835 A | 5/1988 | Sandhaus |
| 4,774,772 A | 10/1988 | Vetter et al. |
| 4,781,701 A | 11/1988 | Geprags |
| 4,834,715 A | 5/1989 | Hanifl |
| 4,874,318 A | 10/1989 | Vetter |
| 4,917,867 A * | 4/1990 | Jensen et al. ................ 422/102 |
| 5,069,670 A | 12/1991 | Vetter et al. |
| 5,100,010 A | 3/1992 | Waters |
| 5,104,379 A | 4/1992 | Nakamura et al. |
| 5,135,496 A | 8/1992 | Vetter et al. |
| 5,135,513 A | 8/1992 | Meyer et al. |
| 5,184,742 A | 2/1993 | DeCaprio et al. |
| 5,403,288 A * | 4/1995 | Stanners .................. 604/241 X |

(List continued on next page.)

FOREIGN PATENT DOCUMENTS

| | | |
|---|---|---|
| EP | 0 022 576 A1 | 1/1981 |
| EP | 0 462 355 A1 | 12/1991 |
| EP | 0 589 379 A1 | 3/1994 |
| EP | 0716860 A2 | 6/1996 |
| EP | 1 034 810 A2 | 9/2000 |
| EP | 1 038 543 A1 | 9/2000 |
| WO | WO 96/14100 | 5/1996 |
| WO | WO 97/20587 | 6/1997 |
| WO | WO 00/59563 | 10/2000 |

*Primary Examiner*—Anhtuan T. Nguyen
(74) *Attorney, Agent, or Firm*—Allen W. Wark; David M. Fortunato

(57) ABSTRACT

A tip cap assembly is provided for positive sealing engagement with the tip of a syringe barrel of a syringe. The tip cap assembly includes an inner cap formed from an elastomeric material dimensioned for sealing engagement with the tip of the syringe barrel. The tip cap assembly further includes an outer cap engaged with the inner cap, and a collar for mounting the tip cap assembly to the syringe barrel. In addition, the outer cap includes a plurality of frangible portions for evidencing tampering and for connecting the outer cap to the collar.

21 Claims, 10 Drawing Sheets

U.S. PATENT DOCUMENTS

| | | |
|---|---|---|
| 5,405,340 A | 4/1995 | Fageol et al. |
| 5,437,650 A | 8/1995 | Larkin et al. |
| 5,624,402 A * | 4/1997 | Imbert .................. 604/111 |
| 5,785,691 A | 7/1998 | Vetter et al. |
| 5,833,653 A | 11/1998 | Vetter et al. |
| 6,027,482 A * | 2/2000 | Imbert .................. 604/240 |
| 6,068,614 A | 5/2000 | Kimber et al. |
| 6,196,998 B1 * | 10/2000 | Jansen et al. ............ 604/111 |

* cited by examiner

SYRINGE AND TIP CAP ASSEMBLY

RELATED APPLICATIONS

The present application is a continuation of application Ser. No. 09/198,978, filed Nov. 24, 1998, which is a continuation-in-part of application Ser. No. 08/847,840, filed Apr. 28, 1997, now U.S. Pat. No. 6,027,482 which is a continuation of application Ser. No. 08/355,447, filed Dec. 12, 1994, U.S. Pat. No. 5,624,402, the disclosure of which is hereby incorporated in its entirety by reference.

FIELD OF THE INVENTION

The present invention generally relates to drug delivery devices and containers, and more specifically relates to a syringe, as well as a tip cap assembly for securely sealing the tip of the barrel of the syringe.

BACKGROUND OF THE INVENTION

Conventional syringes each include a barrel having an open proximal end and an opposed distal. A cylindrical wall extends between the ends and defines a substance retaining chamber. An elongate tip projects from the distal end of the syringe barrel and includes a narrow passage which communicates with the substance retaining chamber of the barrel. A plunger may be inserted into the open proximal end of the syringe barrel for sliding fluid-tight engagement with the cylindrical chamber wall. Sliding movement of the plunger in a distal direction urges fluid in the chamber through the passage in the tip. Conversely, sliding movement of the plunger in a proximal direction draws fluid through the passage in the tip and into the chamber of the syringe barrel.

Conventional syringe barrels typically are made of plastic or glass. Glass exhibits lower gas transmissivity than plastic. Thus, glass syringe barrels are used for medications that are particularly susceptible to interaction with ambient gases. Glass syringe barrels also are preferably used for medications that are pre-filled into the syringe barrel and stored for a considerable period of time prior to use.

Such syringes may further include a needle assembly with a needle cannula having a proximal end, a pointed distal end and a lumen extending axially therethrough. The needle assembly also includes a hub which is engageable with mounting means on the syringe barrel for selectively placing the lumen of the needle cannula in fluid communication with the passage through the tip of the syringe barrel. One prior mounting means includes a luer collar disposed in spaced concentric relationship around the tip of the syringe barrel. The luer collar includes an array of threads for threaded engagement with corresponding structure on the hub of the needle. For example, the luer collar may include an array of internal threads which are engageable with projections extending outwardly from the hub of the needle cannula. Syringe barrels formed from plastic may have the luer collar unitarily molded therewith. However, glass syringe barrels may not be easily formed with a unitary luer collar. Thus, glass syringe barrels and some plastic syringe barrels may have a separately formed luer collar securely mounted to the tip of the syringe barrel. The luer collar may rely upon a slip fit interengagement, a snap fit or other such secure mounting engagement around the tip of the syringe barrel.

Medications that are pre-filled into a syringe barrel must be sealed to prevent contamination or loss of the medication. Seals also prevent health care workers from being needlessly exposed to medications. The prior devices have included stoppers or closures mounted over the tip at the distal end of the syringe barrel to prevent leakage and to avoid contamination of the medication. Prior tip caps have been formed from elastomeric material frictionally and/or resiliently retained in engagement with the tip of the prior syringe barrel. The prior tip cap may be removed from the syringe tip shortly prior to usage of the syringe. The hub of the needle assembly may then be securely engaged with the luer collar or other mounting means adjacent the exposed tip of the syringe barrel. For example, the needle hub may be threadedly engaged within the luer collar such that the lumen of the prior needle cannula communicates with the exposed tip of the prior syringe barrel.

Prior elastomeric tip caps on the ends of pre-filled syringe barrels generally perform well. However, the resiliently and/or frictionally engaged type tip cap may be accidentally disengaged from the tip of the syringe barrel in response to inadvertent forces imposed thereon or due to dimensional changes or instability of the elastomeric seal. Additionally, the vacuum or suction effect created as the prior elastomeric tip cap is removed from the tip of the syringe barrel can lead to the loss of medication and unnecessary personal contact with medication that the tip cap is intended to avoid. Additionally, the prior elastomeric tip cap provides no evidence of tampering or misuse of a pre-filled syringe.

Thus, there has been a need for a syringe, as well as a tip cap, which would eliminate the problems and limitations associated with the prior syringes discussed above, most significant of the problems being evidence of tampering or misuse of a pre-filled syringe.

SUMMARY OF THE INVENTION

In contrast to the prior devices discussed above, it has been found that a syringe particularly suited for evidencing tampering or misuse of a pre-filled syringe can be constructed in accordance with the present invention. Specifically, the syringe of the present invention includes a tip cap which evidences tampering or misuse of the syringe.

The subject invention is directed to a syringe as well as an effective tip cap assembly for the syringe, and to a syringe assembly having a more effectively sealed tip. A syringe in accordance with the subject invention includes a barrel having a proximal end, a distal end and a chamber wall extending therebetween. The chamber wall defines a substance receiving chamber which may be pre-filled with a selected dose of medication in either dry or liquid form, as well as water or diluent used for reconstituting a medicament. The distal end of the syringe barrel includes a tip having a passage extending therethrough. The distal end may further include needle mounting means for selective engagement with mounting structure on a needle cannula. The mounting means may comprise a collar that is either unitarily formed with the syringe barrel or that is securely mounted to the syringe barrel in proximity to the tip. In addition, the collar may be a locking luer type fitting.

The tip cap of the subject invention includes an elastomeric material to form a soft inner cap frictionally and/or resiliently engageable with portions of the tip for sealing the passage through the tip. The tip cap assembly further includes a substantially rigid outer cap engageable with the needle mounting means of the syringe barrel and protectively enclosing the inner cap. The outer cap may be frictionally, resiliently and/or mechanically engaged with the inner cap. Thus, disengagement of the outer cap from the needle mounting means of the syringe barrel may simultaneously disengage the inner cap from the tip of the syringe barrel.

The inner cap and the outer cap may be separately manufactured and assembled to one another after manufacture. Alternatively, the inner cap and the outer cap may be integral with one another. In this regard, the inner or outer cap may define an insert in a mold cavity employing insert molding technology. Alternatively, the inner and outer caps may be formed by coinjection of appropriate materials into the mold cavity of an injection molding apparatus. Still further, the inner and outer caps may be formed respectively by sequential injection molding techniques using a single mold cavity.

The inner and outer caps may be assembled or molded together and subsequently attached to a needle mounting structure unitarily formed at the distal end of a plastic syringe barrel. Alternatively, the inner and outer caps may be assembled or formed together and then engaged with a plastic mounting collar for a glass syringe barrel. The assembled inner and outer caps and the mounting collar engaged therewith may then be securely mounted to the tip of a syringe barrel.

The subject invention may further include a tamper evident means connecting the outer cap to the mounting means. The tamper evident means may comprise a plurality of frangible portions separating the outer cap into a proximal portion and a distal portion.

BRIEF DESCRIPTION OF THE DRAWINGS

The various features, objects, benefits, and advantages of the present invention will become more apparent upon reading the following detailed description of the preferred embodiment(s) along with the appended claims in conjunction with the drawings, wherein like reference numerals identify corresponding components, and:

DETAILED DESCRIPTION OF THE PREFERRED EMBODIMENT

Figure 1:
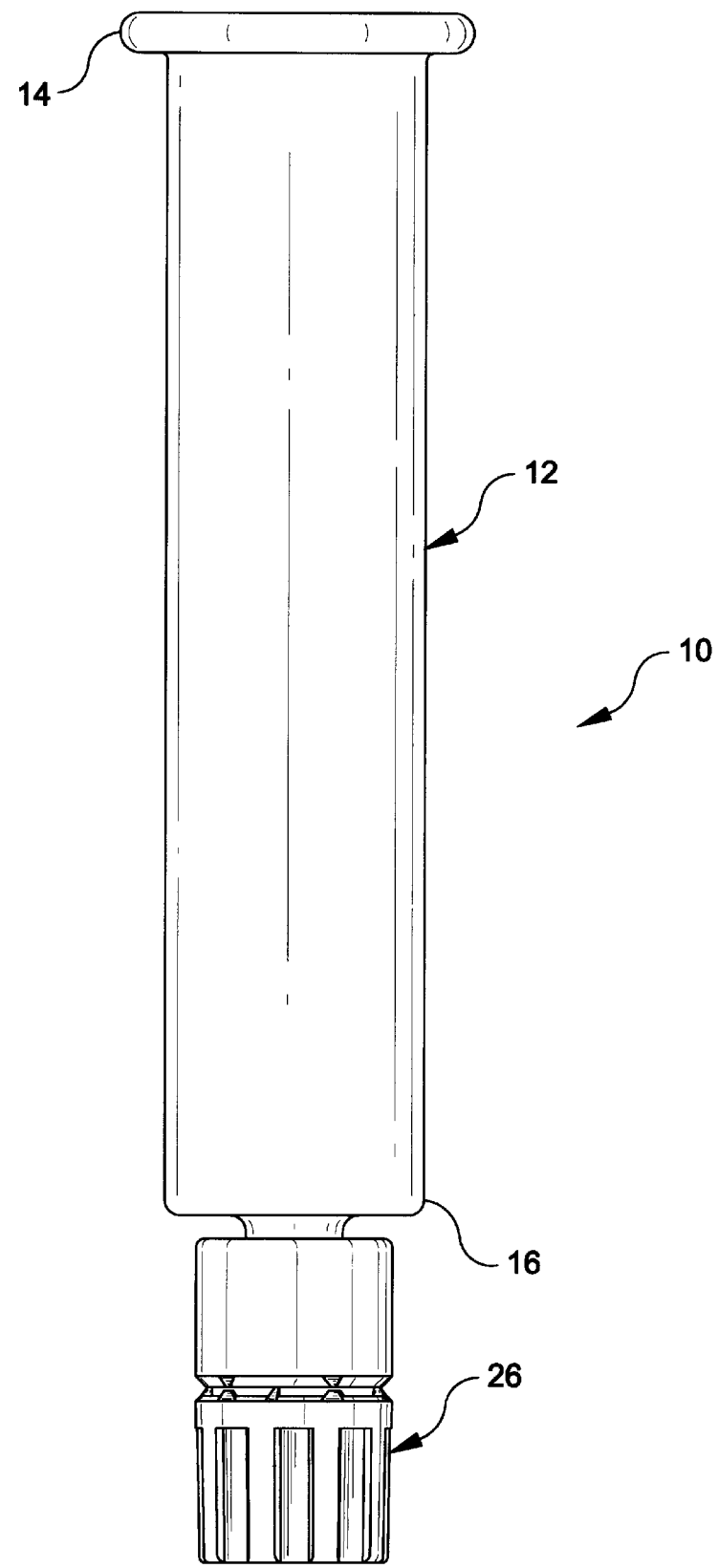
FIG. 1 is a side view of the syringe of the present invention.

The syringe and tip cap assembly of the present invention are illustrated in FIGS. 1 through 8, with the syringe being generally designated 10 and the tip cap assembly being generally designated 26.

As shown in FIGS. 1–5, the syringe 16 includes a syringe barrel 12 unitarily formed from a material, such as glass or plastic, preferably transparent. The syringe barrel 12 includes a proximal end 14, a distal end 16 and a cylindrical wall 18 extending therebetween. The cylindrical wall 18 defines a substance receiving chamber 20 which may be pre-filled with a selected dose of medication in either dry or liquid form, as well as other substances such as water or diluent for use in reconstituting a medicament. The distal end of syringe barrel 12 includes a tip 22 having a passage 24 extending therethrough and communicating with the chamber 20. A plunger rod assembly (now shown) may extend into the proximal end 14 of the syringe barrel 12, and include a stopper, which may slide in fluid-tight engagement inside the cylindrical wall 18 of the chamber 20.

Figure 6:
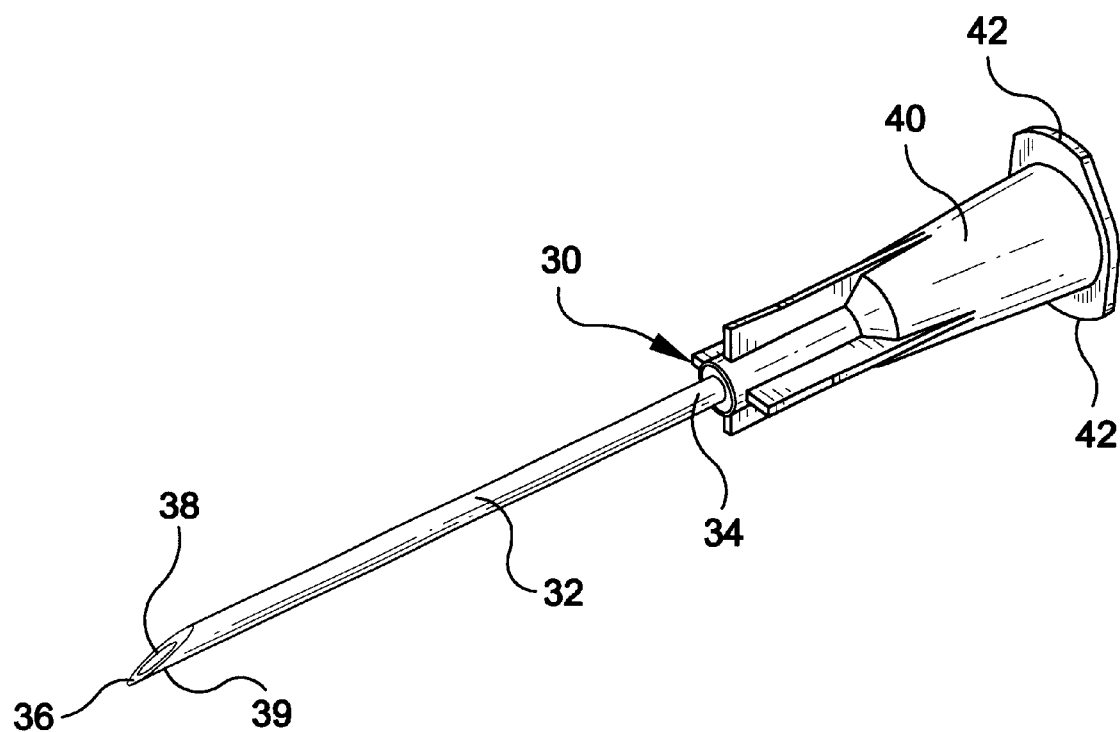
FIG. 6 is an elevational view of a needle assembly useable with the syringe of the present invention.

The syringe barrel 12 may be used with a needle assembly 30 as shown in FIG. 6, with the needle assembly 30 including a needle cannula 32 having a proximal end 34, a distal end 36 and a lumen 38 extending therebetween. The distal end 36 of the needle hub preferably includes a sharpened tip 39. A mounting hub 40 is securely affixed to the proximal end 34 of the needle cannula 32 and includes projections 42 extending therefrom for threaded engagement with a collar. However, it should also be appreciated that the syringe, as well as the tip assembly, of the present invention may be used without a needle assembly, for example, for use as a flush syringe which may be connected to an infusion line or for use in reconstituting a dry medication for connection with a transfer set for a vial drug container.

As noted above, the syringe barrel 12 may be formed from glass, and hence generally does not have an integral collar for engaging the mounting hub 40, particularly the projections 42, of the needle assembly 30. As noted, the needle assembly 30 may be maintained separate from the syringe barrel 12, and may be mounted to the syringe barrel 12 a short time prior to usage of syringe 10. In this way the syringe barrel 12 may be pre-filled with medication, and stored in its pre-filled condition prior to mounting needle assembly 30 thereto. To prevent contamination or leakage of medication stored in syringe. barrel 12, a tip cap assembly 26 is provided on the tip 22 of the syringe barrel 12.

Referring to FIGS. 1–5, and FIGS. 7 and 8 for greater detail, the tip cap assembly 26 preferably includes a collar 44, an inner cap 56 and an outer cap The collar 44 is selectively engageable over the tip 22 of the syringe barrel 12. More particularly, the collar 44 is a generally hollow cylindrical structure having opposed proximal and distal ends 46 and 48, and preferably of the locking luer type fitting. The proximal end 46 of the collar 44 includes an array of inwardly directed projections 50 for frictionally engaging the tip 22 of the syringe barrel 12 and retaining the collar 44 thereon. The distal end 48 of the collar 44 includes an array of internal threads 52 dimensioned and pitched for threaded engagement by the projections 42 of the mounting hub 40 on the needle assembly 30. Thus, the proximal end 46 of the collar 44 can be urged in a proximal direction over the tip 22 of syringe barrel 12. In this way, the mounting projections 50 will deflect slightly, and move into a groove 54 formed in the tip 22 of the syringe barrel 12 to frictionally engage the tip 22 to resist separation of the collar 44 from the syringe barrel 12. Thus, the mounting hub 40 of the needle assembly 30 may then be threadedly engaged with the collar 44 to place and secure the lumen 38 of the needle cannula 32 in communication with the passage 24 through the tip 22, and further in communication with the chamber 20 of the syringe barrel 12.

As noted above, the needle assembly 30 may be maintained separate from the syringe barrel 12, and may be mounted to the syringe barrel 12 a short time prior to usage of the syringe 10. In this way, the syringe barrel 12 may be pre-filled with medication, and stored in its pre-filled condition prior to mounting the needle assembly 30 thereto.

Figure 2:
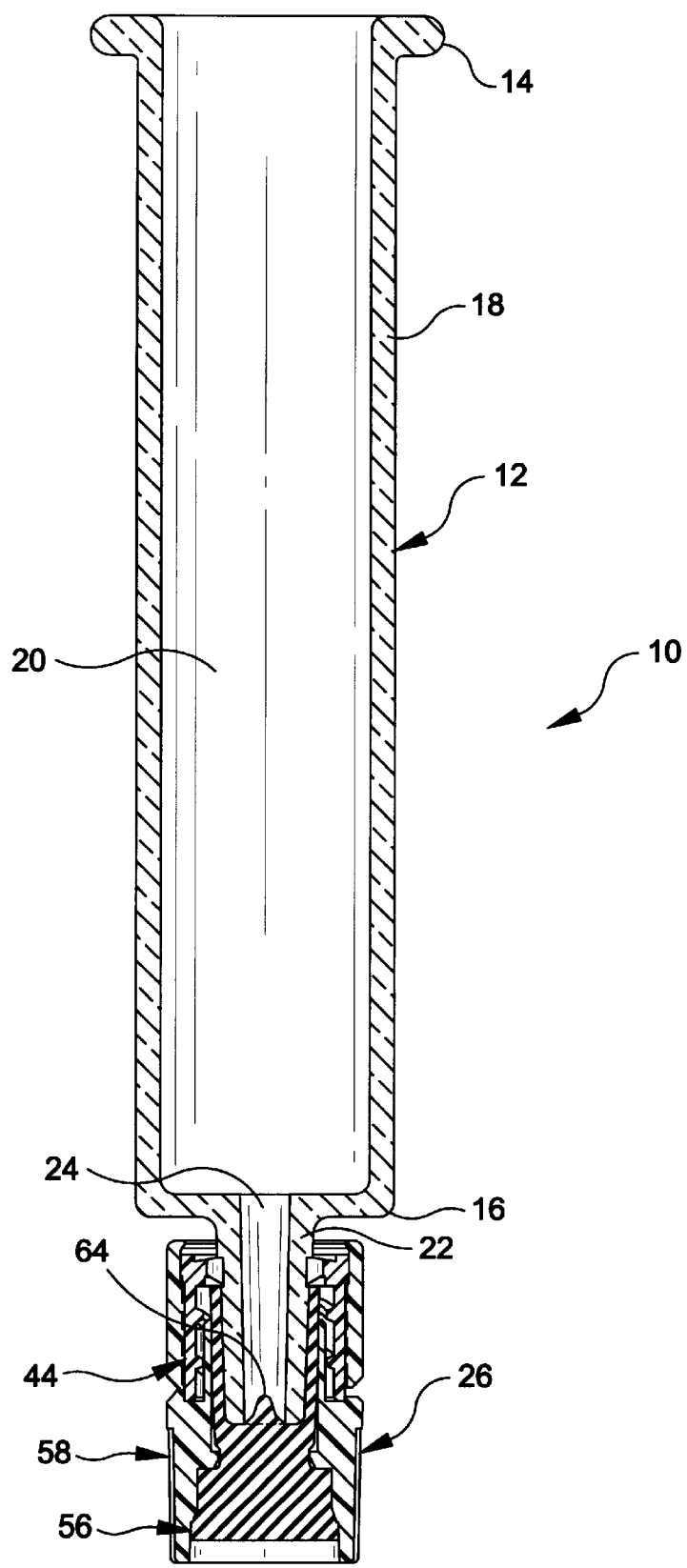
FIG. 2 is a cross-sectional side view of the syringe of the present invention illustrated in FIG. 1.
Figure 3:
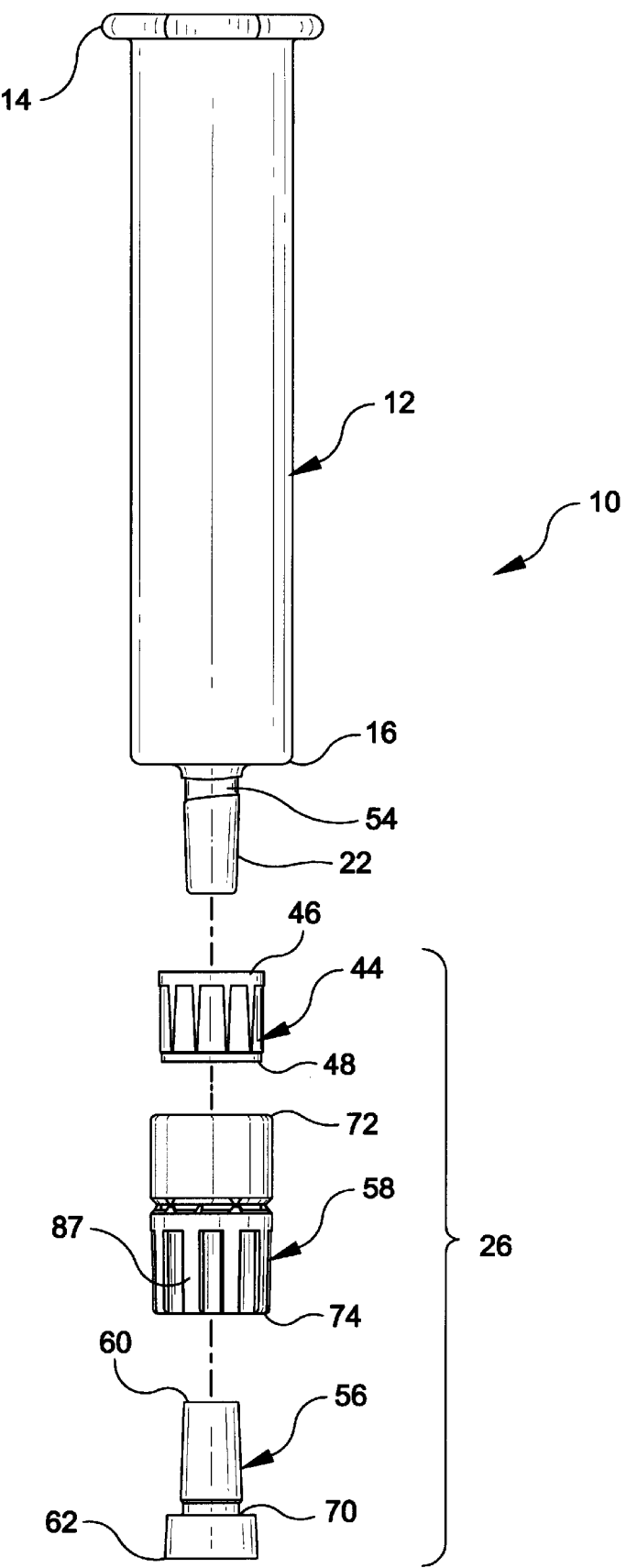
FIG. 3 is an exploded side view of the syringe of the present invention.
Figure 5:
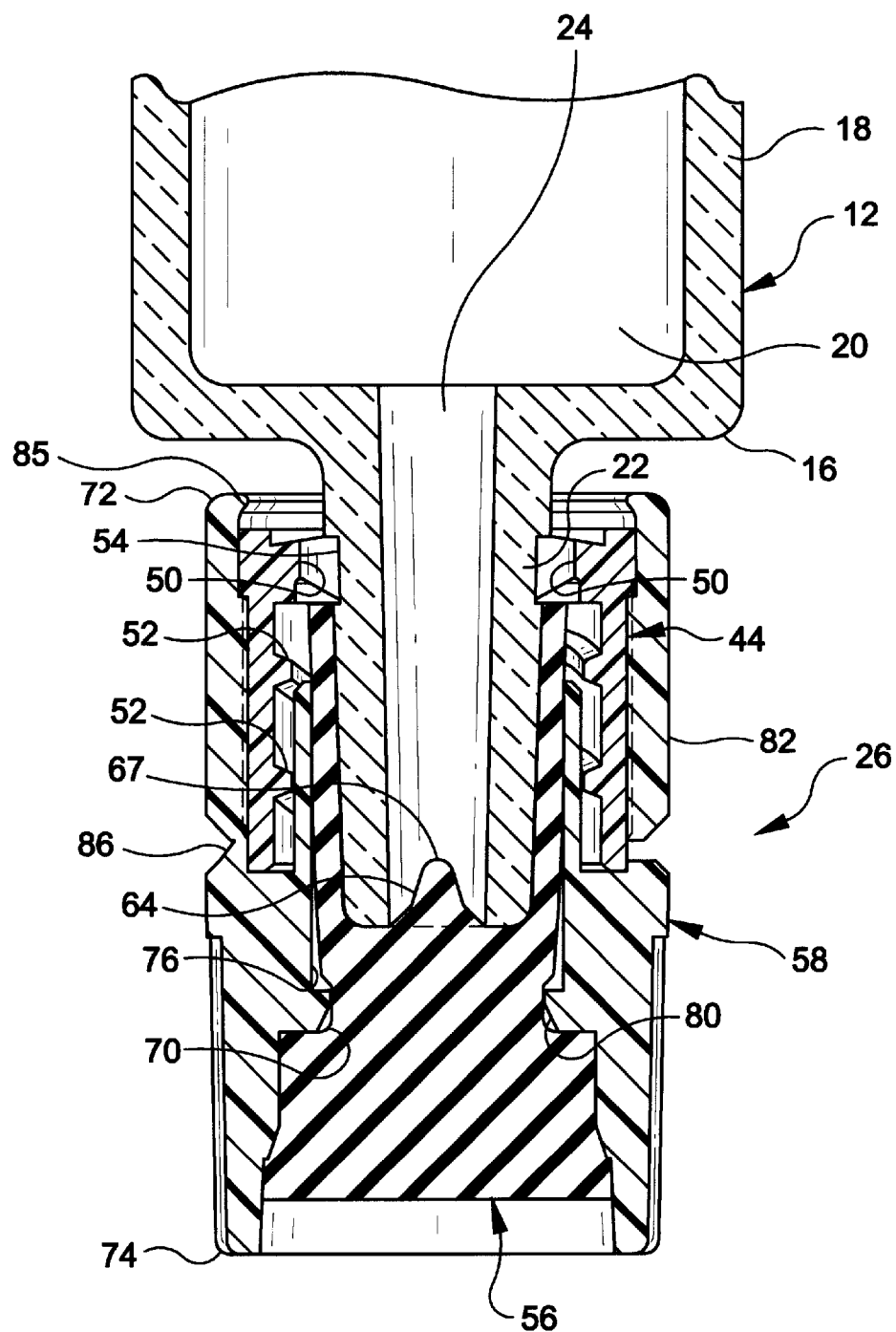
FIG. 5 is an enlarged, cross-sectional side view of the tip cap assembly of the present invention is a fully assembled condition.
Figure 8:
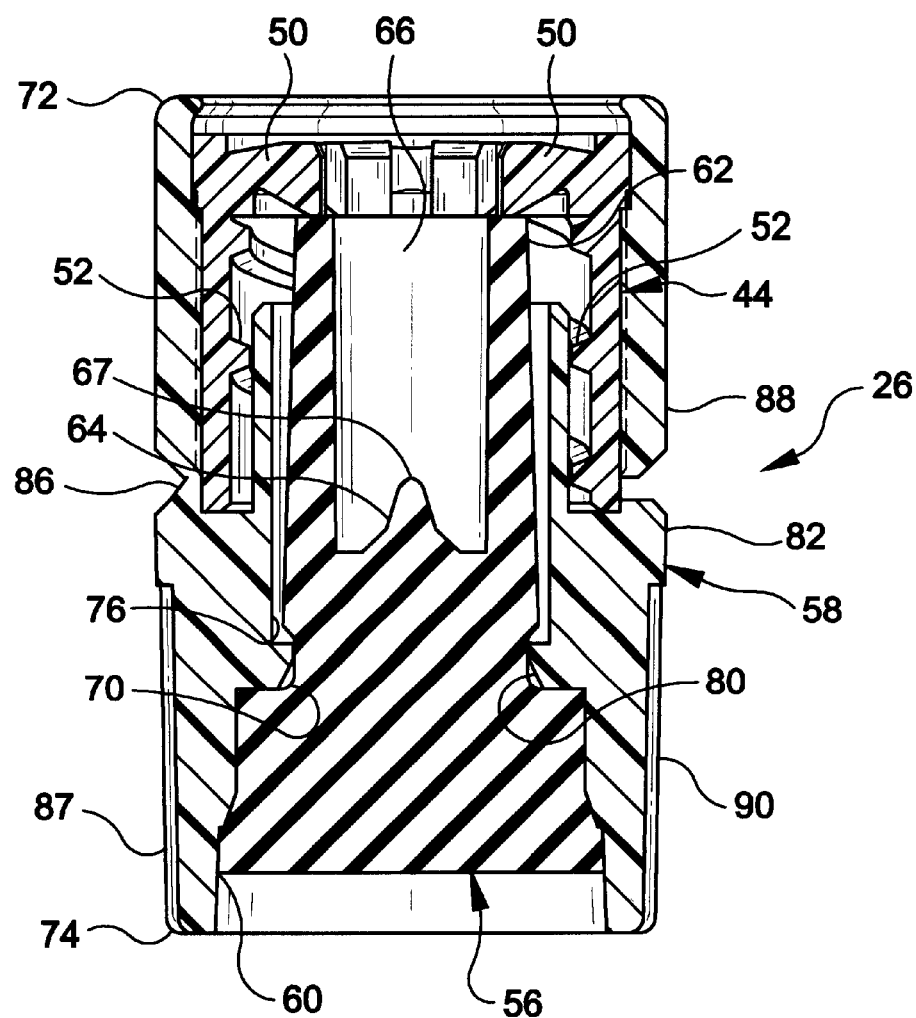
FIG. 8 is an enlarged, cross-sectional side view of the tip assembly illustrated in FIG. 7.

The inner cap 56, as shown most clearly in FIGS. 2 and 5, seals the tip 22 of the syringe barrel 12 to prevent contamination or leakage of the substance stored in the syringe barrel 12 and is unitarily molded from an elastomeric material to form a soft inner cap including opposed proximal and distal ends 60 and 62 respectively. The portions of the inner cap 56 extending proximally from distal end 62 define a tip-engaging portion 64 having a cavity 66 dimensioned to tightly and resiliently engage passage 24 in the tip 22 of the syringe barrel 12. This preferred embodiment preferably includes a stopper portion 67 projecting proximally from the portions of the tip-engaging portion 64 and defines the innermost end of the cavity 66 (FIG. 8). The stopper portion 67 is disposed and dimensioned to come in contact with and seal the end of the passage 24 of the tip 22 of the syringe barrel 12 for further enhancing the sealing ability of the inner cap 56.

The inner cap 56 further includes an annular undercut 70 extending around the outer periphery thereof at a location spaced from distal end 62 of the inner cap 56. The undercut 70 defines an outside diameter of the inner cap 56.

Figure 4:
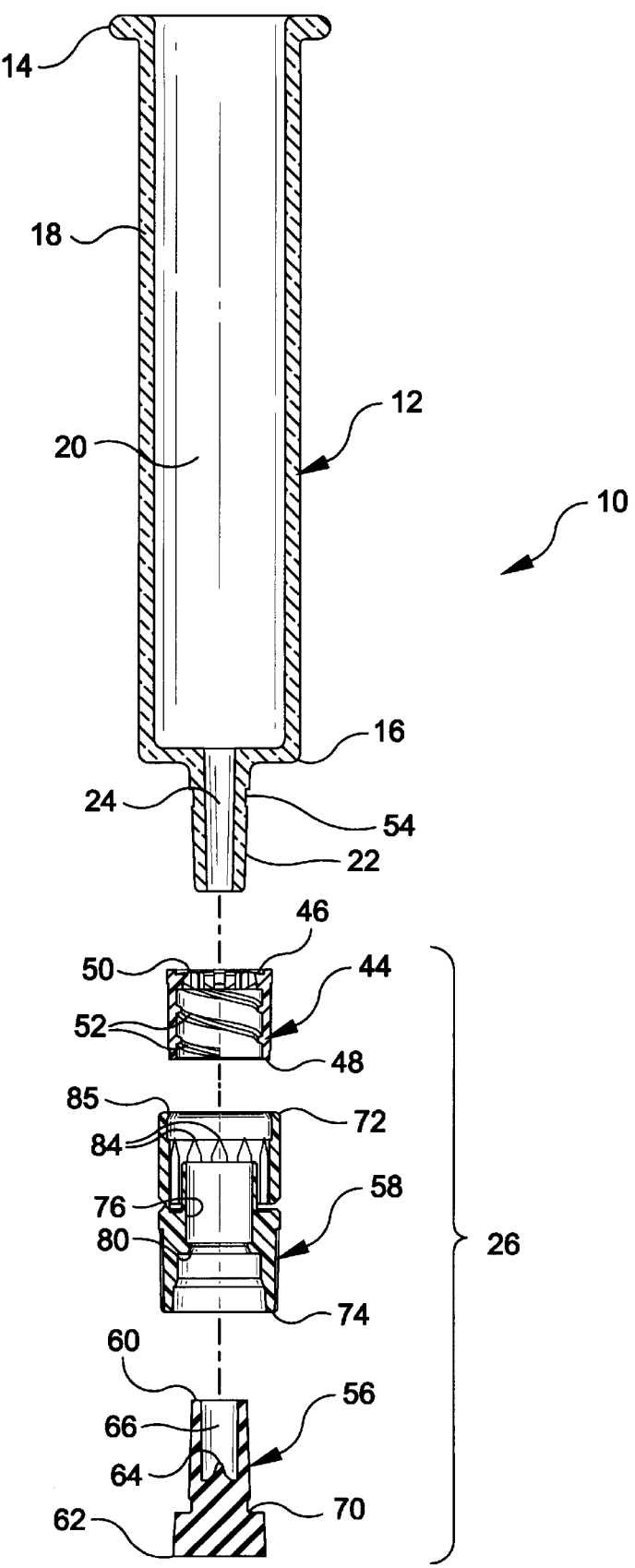
FIG. 4 is an exploded, cross-sectional side view of the syringe of the present invention illustrated in FIG. 3.
Figure 7:
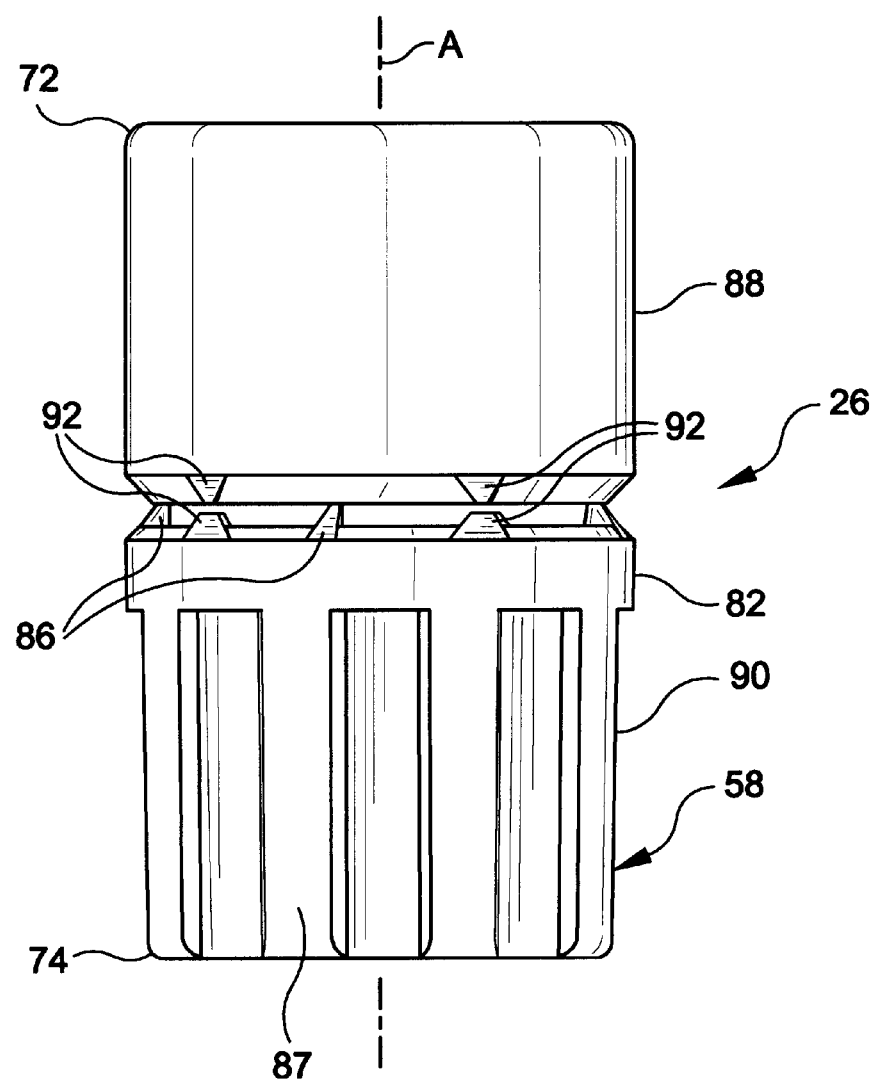
FIG. 7 is an enlarged, side view of the tip cap assembly of the present invention.

The outer cap 58, as shown most clearly in FIGS. 4, 7 and 8, is a generally tubular member unitarily formed from a thermoplastic material, and preferably rigid. The outer cap 58 includes opposed proximal and distal ends 72 and 74 respectively and a stepped aperture 76 extending entirely therethrough. Portions of the aperture 76 adjacent the distal end 74 define a major inside diameter which is approximately equal to the major outer diameter of the inner cap 56.

The stepped aperture 76 further includes an inwardly extending annular rib 80 disposed and dimensioned to engage in the annular undercut 70 in the inner cap 56. More particularly, the annular rib 80 is spaced a distance from the distal end 74, which is approximately equal to or greater than the distance between the undercut 70 and the distal end 62 of the inner cap 54. The annular rib 80 also defines an inside diameter which is approximately equal to the outside diameter defined by the undercut 70 in the inner cap 56. The distal portions of the annular rib 80 are chamfered to facilitate deflection of inner cap 56 during assembly of the inner cap 56 and the outer cap 58, as explained further herein.

The portions of the stepped aperture 76 extending between the annular rib 80 and the proximal end 72 of outer cap 58 define an inside diameter which is greater than the outside diameter of the tip-engaging portion 64 of the inner cap 56, such that the tip-engaging portion 64 can be loosely engaged therein with room for expansion as the entire tip cap assembly is urged over tip 22, as explained further below.

Figure 9:
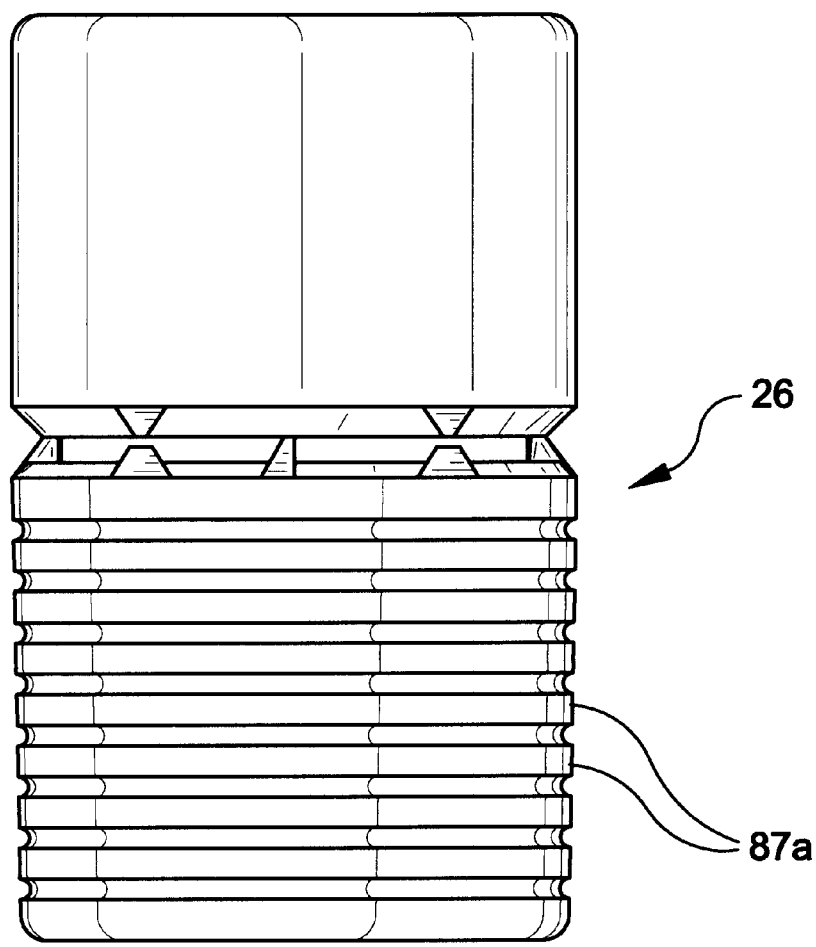
FIG. 9 is a side view of an alternative embodiment of the tip cap assembly of the present invention.

An intermediate portion of the outer cap 58 extends distally from the proximal end 72 and is dimensioned to be insertable into the collar 44. An exterior portion of the outer cap 58 extends proximally from the distal end 74 and is dimensioned to form a sleeve 82 extending over the collar 44 to retain the collar therein. In addition, the interior of the proximal end 72 of the sleeve 82 includes a plurality of ribs 84 for limiting relative axial movement between the sleeve and the collar 44. In addition, the proximal end of the outer cap includes a projecting edge in the form of a lip 85 dimensioned and configured to grip the proximal end 46 of the collar 44, to preferably provide a snap-on fit. In addition, the distal end 74 of the outer cap 58 includes a plurality of external ribs 87 which are dimensioned and configured to facilitate manual gripping of the outer cap 58, for example vertically oriented ribs as most clearly shown in FIGS. 1, 3 and 7, or horizontally oriented ribs 58a as shown in FIG. 9. In this way, the outer cap 58 can be removed by either tilting it relative to the axis A of the tip cap assembly 26 or by rotating it relative to the collar 44 about the axis A.

The inner and outer caps 56 and 58 are assembled by urging the proximal end 60 of the inner cap 56 in a proximal direction into the distal end 74 of the outer cap 58. The tip-engaging portion 64 of the inner cap 56 will engage the chamfer of the inwardly extending rib 80 on the outer cap 58 and will be deflected inwardly. Further advancement of the inner cap 56 into the outer cap 58 will cause the undercut 70 to align with the annular rib 80. The inner cap 56 then will resiliently return toward an undeflected condition, such that the annular rib 80 of the outer cap 58 is trapped in the undercut 70 to substantially prevent further axial movement between the inner and outer caps 56 and 58 respectively.

The assembled inner and outer caps 56 and 58, particularly the sleeve 82, can then be engaged with the collar 44 as shown in FIGS. 5 and 8 by sliding the sleeve 82 of the outer cap 58 over the collar 44, with the lip 85 dimensioned to snuggly hold the collar 44 therein with the ribs 84 preventing rotation of the collar 44 relative to the sleeve 82, and the tip cap assembly 26 can be urged onto the tip 22 of syringe barrel 12 as shown in FIGS. 2 and 5. The projections 50 on the proximal end 46 of the collar 44 will deflect and engage the tip 22 and/or the groove 54 for securely retaining the collar 44 and the inner and outer caps 56 and 58 on the tip 22. Simultaneously, the tip-engaging portion 64 of the inner cap 56 will sealingly engage the tip 22. In this regard, the tip-engaging portion 64 will resiliently engage the outer circumferential portions of the tip 22, while the stopper portion 67 will pass into and sealingly engage the passage 24 through the tip 22.

The engagement of the outer cap 58 with the collar 44, particularly the sleeve 82 over the collar 44, holds the collar 44 and the inner and outer caps 56 and 58 in place and prevents inadvertent separation of the inner cap 56 from its sealing engagement with the tip 22 of the syringe barrel 12, with the ribs 84 preventing relative rotation between the collar 44 and the outer cap 58, particularly the sleeve 82.

As noted above, misuse of or tampering with medication pre-filled in the syringe barrel 12 should be guarded against. To provide such tamper evidence, the sleeve 82 includes frangible portions 86 spaced circumferentially along the interface separating the outer collar 58 into a proximal portion 88 and a distal portion 90. The frangible portions 86 of the outer cap 58 are, for example, angularly situated about the axis A of the outer cap 58 so that they have some angular and radial strength but are axially compressible. These frangible portions 86 are of pyramidal shape and frangible so that the outer cap 58 can be fractured or broken by either tilting or twisting to remove the inner cap, along with the distal portion 90 of the outer cap 58, from the tip 22 of the syringe barrel 12. In addition, severance of the frangible portions in response to initial separation of the inner and outer caps 56 and 58 from the collar 44 serves to provide integral and unmistakable evidence of tampering with the syringe barrel 12 and the medication therein. In this way, the tip 22 of the syringe barrel 12 can be accessed readily by merely tilting or rotating the outer cap 58 relative to the collar 44 to allow the user to fit the needle assembly 30 to the collar 44.

In addition, the sleeve 82 of the outer cap 58 includes a plurality of paired spacer blocks 92, for example, preferably alternating with the frangible portions 86. These pairs of spacer blocks 92 are of trapezoidal shape and taper axially toward each other. The blocks 92 partially bridge the gap formed between the axially spaced edges of the proximal and distal portions 88 and 90, and have outer ends that touch or are axially very closely juxtaposed with each other.

Thus the tip cap assembly 26 formed by the collar 44, and the inner and outer caps 56 and 58, is fitted over the tip 22 of the syringe barrel 12 by simply axially pushing it until the projections 50 deflect slightly and frictionally engaging tip 22 into the groove 54 of the syringe barrel 12 to resist separation of the collar 44 from the syringe barrel 12. During such installation the blocks 92 bear axially towards each other so that no significant force is transmitted through the frangible portions 86 and consequently prevent breaking of them during assembly.

Figure 10:
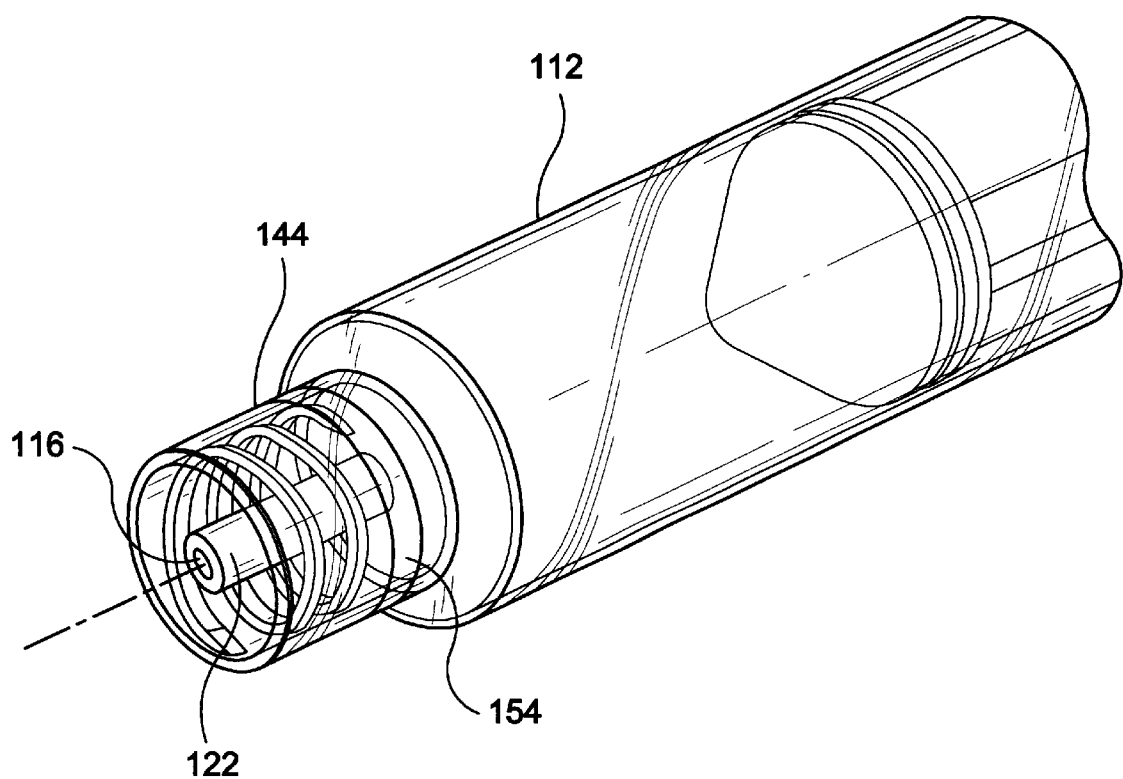
FIG. 10 is a perspective view similar to FIG. 5 but showing a syringe barrel having a unitary collar.

As illustrated in FIGS. 1–9, the cap assembly 26 includes a thermoplastic collar 44 that is mountable to the tip 22 of a glass syringe barrel. However, a tip cap assembly in accordance with the present invention can be employed with similar advantages to a thermoplastic syringe barrel having a collar molded thereto. In this regard, FIG. 10 shows a thermoplastic syringe barrel 112 having a distal end 116 with a tip 122 projecting therefrom. A collar 144 projects unitarily from the distal end 116 in spaced concentric relationship about the tip 122. The tip cap assembly, including only the inner and outer caps 56 and 58 as identified and described above, is engageable with the collar 144 such that the elastomeric inner cap 56 is sealingly engageable with the tip 122 of the syringe barrel 112 until locking into a groove 154. Unintended separation of the inner cap 56 from the tip 122 is substantially prevented by the sleeve 82 surrounding the collar and locking into the groove 154 formed in the outer surface of the collar 144 to secure the outer cap 58, as well as the inner cap 56, to the tip 122 of the syringe barrel 112. However, the tip 122 can still be accessed readily by either tilting or rotating the outer cap 58 for disengagement from the collar 144.

While the preferred embodiments of the present invention have been described so as to enable one skilled in the art to practice the device of the present invention, it is to be understood that variations and modifications may be employed without departing from the concept and intent of the present invention as defined in the following claims. For example, the inner and outer caps need not be separate parts that are assembled after manufacture. Rather, the inner and outer caps may be simultaneously molded using injection technology, co-injection technology or sequential injection technology. Alternatively, the inner cap or the outer cap may define an insert in an injection molding cavity in which the other of the inner and outer caps is molded. Accordingly, the preceding description is intended to be exemplary and should not be used to limit the scope of the invention. The scope of the invention should be determined only by reference to the following claims.

What is claimed is:

1. A tip cap assembly for use with a syringe barrel having a substance receiving chamber and a distally projecting tip with a fluid passageway extending therethrough, said tip cap assembly comprising:
    a collar securely engageable around the tip;
    an inner cap sealingly engageable with the tip, said inner cap being formed of an elastomeric material;
    a rigid outer cap securely disposed around said inner cap and engageable with said collar;
    tamper indicator means provided on said outer cap for indicating separation of at least a portion of said outer cap from said collar; and
    said assembly being configured so that said inner cap sealingly engages the tip when said collar is securely engaged around the tip to seal a substance contained in the chamber of the syringe barrel, and said inner cap is disengageable from the tip in response to disengagement of said outer cap from said collar.

2. The tip cap assembly of claim 1, wherein said collar includes needle mounting means for releasably engaging a needle assembly, said outer cap being releasably engageable with said needle mounting means of said collar.

3. The tip cap assembly of claim 2, wherein the needle mounting means of said collar comprises an array of threads.

4. The tip cap assembly of claim 1, wherein at least a portion of said outer cap is disengageable from said collar by breaking said tamper indicator means.

5. The tip cap assembly of claim 1, wherein said inner cap is formed from an elastomeric material, and wherein said outer cap is formed from a rigid plastic material.

6. The tip cap assembly of claim 1, wherein said tamper indicating means includes a plurality of frangible portions separating said outer cap into a proximal portion and a distal portion, with the proximal portion surrounding said collar.

7. The tip cap assembly of claim 6, wherein said tamper indicating means includes a plurality of spacer blocks at least partially bridging a gap between said proximal portion and said distal portion of said outer cap to avoid movement and breaking of the frangible portions.

8. The tip cap assembly of claim 1, wherein said outer cap further includes means dimensioned and configured for gripping the proximal end of the collar.

9. The tip cap assembly of claim 1, wherein said proximal end of said inner cap includes a side wall defining a cavity for accepting said tip.

10. The tip cap assembly of claim 1, wherein said outer cap further includes means for limiting relative movement between said proximal portion of said outer cap and said collar.

11. A syringe with a syringe barrel having a substance receiving chamber and a distally projecting tip with a fluid passage extending therethrough and a tip cap assembly attached to the projecting tip, said tip cap assembly comprising:
    a collar concentrically surrounding the tip, the collar including an array of internal threads for threadingly engaging a needle hub;
    a resilient inner cap having opposed proximal and distal ends, said proximal end defining a tip engaging portion for sealingly engaging the tip to seal a substance contained in the chamber of said syringe barrel;
    a rigid outer cap securely engaged around at least a portion of said inner cap, said outer cap having a sleeve engageable with the collar such that said outer cap securely and releasably retains said collar therein and said inner cap in sealing engaged with the tip; and
    tamper indicator means provided on said sleeve of said outer cap for indicating separation of said outer cap from said collar.

12. The syringe of claim 11, wherein said outer cap further includes means dimensioned and configured for gripping the proximal end of the collar.

13. The syringe of claim 11, wherein said outer cap further includes means for limiting rotation between said proximal portion of said outer cap and said collar.

14. The syringe of claim 11, wherein said outer cap further includes means for limiting relative movement between said proximal portion of said outer cap and said collar.

15. The syringe of claim 11, wherein one of said inner and outer caps includes an annular rib, and wherein the other of said inner and outer caps comprises an annular groove engaged with said annular rib.

16. The syringe of claim 11, wherein said proximal end of said inner cap includes a side wall defining a cavity for accepting said tip.

17. The syringe of claim 11, wherein said tamper indicating means includes a plurality of frangible portions separating said outer cap into a proximal portion and a distal portion, with the proximal portion surrounding said collar.

18. The syringe of claim 17, wherein said tamper indicating means includes a plurality of spacer blocks at least partially bridging a gap between said proximal portion and said distal portion of said outer cap.

19. The syringe of claim 11, wherein said inner cap is formed from an elastomeric material, and wherein said outer cap is formed from a rigid plastic material.

20. A syringe comprising:

a syringe barrel having a substance receiving chamber and a tip projecting from a distal end of said syringe barrel with a fluid passage extending through said tip;

a collar concentrically surrounding the tip;

a resilient inner cap having opposed proximal and distal ends, said proximal end defining a tip engaging portion for sealingly engaging the tip to seal a substance contained in the chamber of said syringe barrel;

a rigid outer cap securely engaged around at least a portion of said inner cap, said outer cap having a sleeve engageable with the collar such that said outer cap securely and releasably retains said collar therein and said inner cap in sealing engaged with the tip; and tamper indicator means provided on said sleeve of said outer cap for indicating separation of said outer cap from said collar.

21. The syringe of claim 20, wherein said collar is either releasably attached to the distal end of said syringe barrel or integrally formed thereon.

* * * * *